US009011367B2

United States Patent
Humbert et al.

(10) Patent No.: US 9,011,367 B2
(45) Date of Patent: Apr. 21, 2015

(54) DEVICE AND METHOD FOR INJECTING PULSED STEAM INTO A HUMAN OR ANIMAL VESSEL E.G. A VEIN

(75) Inventors: Sophie Humbert, Arbusigny (FR); René Milleret, Montpellier (FR); Sébastien Lugbull, Seyssel (FR)

(73) Assignee: Cermavein, Archamps (FR)

( * ) Notice: Subject to any disclaimer, the term of this patent is extended or adjusted under 35 U.S.C. 154(b) by 0 days.

(21) Appl. No.: 13/983,833

(22) PCT Filed: Feb. 7, 2012

(86) PCT No.: PCT/EP2012/052071
§ 371 (c)(1),
(2), (4) Date: Sep. 18, 2013

(87) PCT Pub. No.: WO2012/107456
PCT Pub. Date: Aug. 16, 2012

(65) Prior Publication Data
US 2014/0005594 A1    Jan. 2, 2014

(30) Foreign Application Priority Data

Feb. 7, 2011 (WO) ................. PCT/EP2011/051765

(51) Int. Cl.
*A61M 37/00* (2006.01)
*A61B 18/04* (2006.01)
*A61B 18/00* (2006.01)

(52) U.S. Cl.
CPC ............... *A61M 37/00* (2013.01); *A61B 18/04* (2013.01); *A61B 2018/00404* (2013.01); *A61B 2018/046* (2013.01); *A61B 2018/048* (2013.01); *A61B 2018/00422* (2013.01); *A61B 2018/00577* (2013.01)

(58) Field of Classification Search
CPC ...................... A61B 2018/00017; A61B 18/04
USPC ................... 604/23, 24, 25, 26, 114
See application file for complete search history.

(56) References Cited

U.S. PATENT DOCUMENTS

| 4,191,185 | A  | * | 3/1980 | Lemieux ........................ 604/533 |
| 6,261,312 | B1 | * | 7/2001 | Dobak et al. .................. 607/105 |
| 2002/0177846 | A1 | * | 11/2002 | Mulier et al. .................. 606/27 |

(Continued)

FOREIGN PATENT DOCUMENTS

| WO | WO-97/18765 | 5/1997 |
| WO | WO-00/11927 | 3/2000 |

(Continued)

*Primary Examiner* — Nicholas Lucchesi
*Assistant Examiner* — Anh Bui
(74) *Attorney, Agent, or Firm* — Miller, Matthias & Hull LLP (57) ABSTRACT

The purpose of the invention is to develop an improved device for injecting pulsed steam into a human or animal vessel (e.g. veins), especially tributaries and perforating veins to treat them through thermofibrosis. The device of the invention includes a water pulse generator that produces micro pulses of pressurized sterile water; a hand piece that transforms pulses of water coming from the generator into pulses of steam; an endoluminal catheter with a tubular part for delivering the steam into the vessel; connection means between the hand piece and the endoluminal catheter; and a programmable central processing unit (cpu) to control the water pulse generator and the hand piece.

4 Claims, 5 Drawing Sheets

(56) References Cited

U.S. PATENT DOCUMENTS

2003/0171721 A1* 9/2003 Enomoto et al. .............. 604/247
2003/0191460 A1* 10/2003 Hobbs et al. .................... 606/15
2008/0281267 A1* 11/2008 Mehier ......................... 604/113

FOREIGN PATENT DOCUMENTS

WO WO-02/069821 A1 9/2002
WO WO-2009/009398 A1 1/2009

* cited by examiner

FIG. 7

DEVICE AND METHOD FOR INJECTING PULSED STEAM INTO A HUMAN OR ANIMAL VESSEL E.G. A VEIN

CROSS-REFERENCE TO RELATED APPLICATIONS

This application is a U.S. national stage filing under 35 USC §371 of International Patent Application No. PCT/EP2012/052071 filed on Feb. 7, 2012, which claims priority under the Paris Convention and 35 USC §119 to International Patent Application No. PCT/EP2011/051765 filed on Feb. 7, 2011.

FIELD OF THE DISCLOSURE

The invention concerns a new device for treating pathological venous or arterio-venous diseases, in particular varicose veins, hemorrhoids, arterio-venous shunts or other vascular malformations, by injecting steam via the endoluminal route, and more particularly for treating tributaries and perforators veins through endovenous occlusion by thermofibrosis with the injecting steam. More precisely, the invention concerns a device for injecting pulsed steam into a human or animal vein.

BACKGROUND OF THE DISCLOSURE

Patients with Chronic Superficial Venous Insufficiency (CSVI) usually present reflux in one or several saphenous trunks, and bulging varicose tributaries and perforators.

Saphenous trunks can be removed by surgery, chemical or thermal ablation.

Concerning thermal ablation of saphenous trunk, reference is made to U.S. Pat. No. 7,753,871-B which discloses a Steam Vein Sclerosis (SVS) device for delivering thermal energy to the venous wall, which results in vein wall fibrotic retraction and its subsequent definitive occlusion or obliteration. Thermal or steam ablation combines the advantages of thermal and chemical ablation. Steam ablation of saphenous trunks has been clinically used for several years with success. The device heats sterile water into steam and delivers the steam into the vein for coagulation of the vein in patients with superficial venous reflux. The steam heats the vein wall transferring thermal energy that raises the temperature of the vascular wall. The thermal energy destroys the intima and causes contraction and thickening of the collagen fibers within the adventitia and especially the media. The diameter of the vein is thus greatly reduced by contraction and thickening of collagen fibrils and also by the spasm induced by the increased temperature. These phenomena result in the occlusion of the venous lumen. Such a concept is faster and simpler and allows a homogenous diffusion of the heat. Moreover, pulsated steam is the best way to convey energy to tissues: it is an excellent heat conductor and avoids carbonization encountered with other thermal approaches. The device is composed of equipment and disposables and consists in 3 main parts:

a cold water pulse generator that produces micro pulses (80 µl) of pressurized sterile water. The generator is composed of a pneumatic piston, a hydraulic pump and a sterile water flask. The pistons produce two phases: the filling up of the hydraulic pump with sterile water and the injection of this sterile water in the hand-piece/pipe.
  a hand piece/pipe that transforms pulses of water in pulses of steam. The heating element is incorporated into the hand piece, close to the distal end, allowing minimal energy loss.
  an endovenous metallic microtube for distributing the steam into the vein.

In practice, the injection unit is in addition combined with a water storage bag. The microtube for distributing the steam into the vein of internal diameter equal to 150 µm and external diameter equal to 350 µm. This microtube is connected to the distal end of the hand piece by any appropriate means. The microtube has transverse openings on a blunt end or a central opening on a non blunt end. The vein to be treated is punctured using a needle positioned in a small catheter about 5 cm long, the surface of which has been Teflon® treated, the needle being withdrawn after inserting the catheter at the surface of the skin. The microtube is introduced into the catheter until the distal end of the microtube reaches the end of the vein to be treated. The generator then sends pulses of cold water into the hand piece, which transforms these pulses into steam at a temperature of about 200° C. and the steam then passes through the microtube to its distal end. Using the markings on the surface of the microtube, the operator progressively withdraws the microtube giving one or more pulses per centimeter depending on the diameter of the vessel.

The means of distributing the steam within the vessels (catheter) described in U.S. Pat. No. 7,753,871-B are adapted to saphenous veins but are not optimized to non-saphenous veins. The catheter used for saphenous trunks obliteration cannot be safely and efficiently used to treat non-saphenous veins like tributaries and perforators because of the length (45 to 60 cm) and low flexibility (has a metallic core) of the current catheter. It is not suitable for veins which are short, very tortuous and with a fragile wall (easy to be perforated) like tributaries and perforators veins. Moreover, the delivery of 70-80 µl water pulses in the SVS device according to U.S. Pat. No. 7,753,871-B is not systematically adapted to all tributaries, specifically to the ones closed to the skin and for smaller veins (tributaries can have smaller diameters compared to saphenous). Finally, the reduction cost of the SVS device for treating non-saphenous veins, is required.

Treatments of non-saphenous varicose veins are currently carried out using 2 techniques:

Ambulatory phlebectomy: removing the vein through small incisions using a "hook", usually under local or tumescent anesthesia.
    1. This process is time consuming
    2. It is often difficult to remove all the veins, especially if they are adhering to the skin, as in areas of lipodermatosclerosis.
    3. Some pigmentation of the scars may occur.
    4. Phlebectomy remains a relatively invasive method that is not easily accepted by patients as it is painful and surgically wounded. And it can be performed only in a surgical setting (operating room).
  Foam sclerosis consists in injecting in the vein a sclerosing agent mixed with air or another gas, usually $CO_2$.
    1. On larger veins it is often followed by inflammatory reactions, pain and pigmentation of the skin. Thrombus removal can be necessary to treat these incidents.
    2. Serious adverse events, such as transient ischemic attacks or ischemic strokes, have been reported with foam sclerotherapy
    3. The quantity of foam injected per session is limited (Tegernsee's Consensus, 2006) so several sessions may be necessary, increasing the overall cost of this technique and requiring the patient to undergo several operations.

Thus, there is a need for a better way to treat tributary and perforator varicose veins with a procedure that is less time-consuming and that is minimally invasive and painfulness than phlebectomy, as well as less incidents-prone than foam sclerotherapy.

SUMMARY OF THE DISCLOSURE

The invention aims notably to reach at least one of the following purposes.

The purpose of the invention is to develop an improved device for injecting pulsed steam into a human or animal vessel (e.g. veins), especially tributaries and perforating veins to treat them through thermofibrosis.

Another purpose of the invention is to develop an improved device for injecting pulsed steam into a human or animal vessel (e.g. veins), especially tributaries and perforating veins to treat them through thermofibrosis, said device being reliable and performing.

Another purpose of the invention is to develop an improved device for injecting pulsed steam into a human or animal vessel (e.g. veins), especially tributaries and perforating veins to treat them through thermofibrosis, said device satisfying the requirement of administering safely and therapeutically efficiently steam into the tributaries and perforating veins.

Another purpose of the invention is to develop an improved device for injecting pulsed steam into a human or animal vessel (e.g. veins), especially tributaries and perforating veins to treat them through thermofibrosis, said device being cheap and simple to manufacture.

Another purpose of the invention is to develop an improved device for injecting pulsed steam into a human or animal vessel (e.g. veins), especially tributaries and perforating veins to treat them through thermofibrosis, said device enabling treatment methods with at least one of the following advantages:
1: 5 min with steam instead of 30 min with surgery
2: no need of removal of the vein, since thermofibrosed
3: no pigmentation (due to the surgical removal) since any removal of the vein
4: minimally invasive in this case: percutaneous insertion of the catheter
5: no inflammatory reaction since any chemical agent is delivered
6: all the veins can be treated in only one session. (Generally, when using a sclerosing agent, small volumes of the said chemical agent can be injected because of possible inflammatory reactions.)

In this respect, the invention concerns a device for injecting pulsed steam into a human or animal vessel (e.g. veins) including:
  a water pulse generator that produces micro pulses of pressurized sterile water;
  a hand piece or heating element that transforms pulses of water coming from the generator into pulses of steam;
  an endoluminal catheter for delivering the steam into the vessel;
  connection means between the hand piece and the endoluminal catheter;
  and a programmable central processing unit (cpu) to control the water pulse generator and the handpiece;
wherein
  a. the endoluminal catheter (4) comprises a tubular part (23) which length L (in cm) is comprised between the following ranges (limits included) given in an increasing order of preference: [1; 30], [2; 28], [3; 27], [4; 26], [5; 25], [6; 24], [8; 22], [10; 20];
  b. the tubular part of the endoluminal catheter is made of a flexible, biocompatible, thermically insulating and thermically resistant material, preferably of a non-metallic material, more preferably a polymer;
  c. the distal end of the endoluminal catheter has a terminal and central opening.

In a first embodiment, the connection means comprise a distal coupling part designed to cooperate with a proximal coupling part of the endoluminal catheter, and the proximal coupling part of the endoluminal catheter comprises:
  a terminal flange ring which is the proximal end of the tubular part of the endoluminal catheter,
  as well as a socket through which goes the tubular part of the endoluminal catheter, said tubular part being able to slide in the socket as far as the flange ring be stopped against a sealing joint inside the socket, this latter being made of a non-flexible, biocompatible, thermically insulating and thermically resistant material, preferably of a non-metallic material, more preferably a polymer.

In a second embodiment, the tightness of the connection between the hand piece and the endoluminal catheter can be improved through the use of such a sealing joint included in the connection means.

In a variant, the device according to the invention is characterized in that the connection means comprise a distal coupling part designed to cooperate with a proximal coupling part of the endoluminal catheter, and wherein the proximal coupling part of the endoluminal catheter comprises:
  a socket which is extended by the tubular part of the endoluminal catheter,
  a check-valve preventing any reflux from tubular part of the endoluminal catheter.

Advantageously, at least one of the following characteristics (d) (e) and/or (f) is implemented:
  d. the endoluminal catheter has at least one transversal hole in addition to the terminal and central opening;
  e. the water pulse generator and the hand piece are designed and controlled by the cpu, so that pulses of steam are made from pulses of water which volumes are comprised between 5 and 70 µl, preferably 10 and 50 µl, and can be injected into the vessel at a controlled period comprised between one pulse/0.5 s and one pulse/2 s;
  f. there are decompression means of the steam coming from the hand piece.

The implementation of characteristics (d), (e) and (f) depends on the type/shape, diameter and localization of the vein to be treated.

The transversal hole(s) for the endoluminal [characteristic (d)] is preferable for dilated veins, for example veins presenting pseudo aneurysmal dilatation and/or having a diameter of more than 3 mm. In this embodiment with the transversal hole(s) [characteristic (d)], the endoluminal catheter allow the vapor to exit by the sides of the endoluminal catheter. The transversal hole(s) is (are) designed to allow the treatment of dilated and tortuous veins by a multidirectional dispersion of steam and/or to decrease of at least 10% of the pressure of the water steam, coming from the heating element. The number of holes is preferably comprised between one and eight, preferably between two and four. The diameter of the holes is comprised between 0.05 mm and the internal diameter of the endoluminal catheter. The holes could be on the whole length of the endoluminal catheter, preferably close to the distal end.

Whereas for veins closed to the skin and/or having a diameter equal to or less than 3 mm, at least one of the following characteristics (e) and/or (f) is implemented.

The device according to the invention concerns more particularly human or animal vessels as blood vessels, preferably veins, and more preferably tributaries or perforators veins.

According to a remarkable feature (f) of the invention, the device comprises decompression means of the steam coming from the hand piece, in order to relieve the walls of the veins.

In a preferred embodiment, these decompression means comprise a chamber which is, for example, integral with the connection means. This chamber defines a space which allows the pressure of the water steam, coming from the heating element, to decrease before going through the endoluminal catheter.

Preferably, the decompression chamber is designed so as to induce a decrease comprised between 10% and 50% of the pressure of the water steam, coming from the heating element.

According to an interesting embodiment of the decompression means, the decompression chamber is a tubular coupling part which is assembled in the extension of the hand piece outlet. The decompression chamber (50) includes a tubular part, wherein the steam pulses coming from the hand piece are discharged. The internal diameter ($d_t$) of the tubular part of the decompression chamber is larger than the internal diameter ($d_o$) of the hand piece outlet. For instance, in an increased order of preference, $d_t \geq 1.2 d_o$; $d_t \geq 1.5 d_o$; $d_t \geq 1.8 d_o$; $d_t \geq 2 d_o$; $3 d_o \geq d_t \geq 2 d_o$; $d_t = 2.5 d_o$. Concretely, $d_t$ is e.g. between about 1 to 5 mm, preferably about 2.5 mm.

And the length of said tubular part is comprised, in an increased order of preference about 5 to about 60 mm; about 10 to about 50 mm; about 20 to about 35 mm.

Preferably, the endoluminal catheter has a circular cross-section and an internal diameter (in an increased order of preference) between about 0.05 mm to 2.5 mm, 0.1 mm to 2.0 mm; 0.30 mm to 0.8 mm; 0.40 mm to 0.7 mm, 0.50 mm to 0.60 mm e.g. 0.56 mm Preferably, the outer diameter of the endoluminal catheter is comprised diameter (in an increased order of preference) between about 0.1 mm to 3.0 mm, 0.50 mm to 2.0 mm; 0.60 mm to 1.60 mm; 0.70 mm to 1.40 mm; 0.90 mm to 1.2 mm; 1.0 mm to 1.1 mm, e.g. 1.07 mm.

In a preferred embodiment, the distal end of the endoluminal catheter has a blunt, especially rounded off, shape, which is safer with respect to the risk of tearing/perforating the vessel wall. Advantageously, the radius of curvature of said distal end is comprised between 0.10 mm and 0.85 mm, preferably between 0.20 and 0.30 mm.

In a first embodiment, the device according to the invention is designed so as to be used in a method for treating tributaries consisting in using the device according to the invention, wherein:
 i. the tubular part of the endoluminal catheter is introduced into a patient's vein to be treated and positioned within the section of the vein to be treated through multiple punctures; each of them corresponding to a given segment of vein to be treated;
 ii. several pulses of pressurized overheated steam are delivered consecutively towards the vein, and the surrounding venous tissue that becomes heated and begins to shrink;
 iii. the tubular part of the endoluminal catheter remains active until there has been sufficient shrinkage of the vein;
 iv. the extent of shrinkage of the vein is possibly detected by appropriate detection means, preferably Doppler echography.

In a second embodiment, the device according to the invention is designed so as to be used in a method for treating by direct obliteration, a tortuous perforating vein longer than 2 cm and extending between a superficial vein and a deep vein, wherein:
 i. the tubular part of the endoluminal catheter is introduced under echo guidance in the perforator, at least 2 cm from the deep vein;
 ii. at least 3 pulses of pressurized overheated steam are delivered;
 iii. then the tubular part of the endoluminal catheter is removed of a distance of about 1 cm and 3 other pulses are emitted.

In a third embodiment, the device according to the invention is designed so as to be used in a method for treating by indirect obliteration, a perforating vein of 2 cm long or less and extending between a superficial vein and a deep vein, wherein:
 i. the tubular part of the endoluminal catheter is introduced distally in the superficial vein, guided upward proximal to the perforator;
 ii. the vein is obliterated by delivering at least 3 pulses of pressurized overheated steam, so that the perforator cannot drain in the upward side of the superficial vein;
 iii. the tubular part of the endoluminal catheter is removed downward proximal to the perforator;
 iv. the vein is obliterated by delivering at least 3 pulses of pressurized overheated steam, so that the perforator cannot drain in the downward side of the superficial vein.

In another aspect, the invention relates to a method for treating tributaries consisting in using the device according to the invention, wherein:
 i. the tubular part of the endoluminal catheter is introduced into a patient's vein to be treated and positioned within the section of the vein to be treated through multiple punctures; each of them corresponding to a given segment of vein to be treated;
 ii. several pulses of pressurized overheated steam are delivered consecutively towards the vein, and the surrounding venous tissue that becomes heated and begins to shrink;
 iii. the tubular part of the endoluminal catheter remains active until there has been sufficient shrinkage of the vein;
 iv. the extent of shrinkage of the vein is possibly detected by appropriate detection, preferably Doppler echography.

Preferably, the segments' length is 4 to 12 cm, preferably 6 to 10 cm.

According to a remarkable feature of the invention, a maximum of 6 pulses are delivered at the same catheter location to avoid overheating at this level.

Preferably, local anesthesia is carried out with 5 to 10 cc of anesthetic, infiltrated between the vein and the skin.

In a variant, skin cooling is used, with skin temperatures down to 4/6° C.

In another aspect, the invention relates to a method of applying steam with a catheter for treating perforating veins, by direct or indirect obliteration.

In the embodiment of direct obliteration for a perforator long and tortuous i.e longer than 2 cm: and extending between a superficial vein and a deep vein, said method consists in using the device herein defined, wherein:
 i. the tubular part of the endoluminal catheter is introduced under echo guidance in the perforator, at least 2 cm from the deep vein;
 ii. at least 3 pulses of pressurized overheated steam are delivered;
 iii. then the tubular part of the endoluminal catheter is removed of a distance of about 1 cm and 3 other pulses are emitted.

In the embodiment of indirect obliteration for short perforators, i.e a 2 cm long or less perforating vein extending between a superficial vein and a deep vein, said method consisting in using the device according to claim 1, wherein:
 i. the tubular part of the endoluminal catheter is introduced distally in the superficial vein, guided upward proximal to the perforator;

ii. the vein is obliterated by delivering at least 3 pulses of pressurized overheated steam, so that the perforator cannot drain in the upward side of the superficial vein;
iii. the tubular part of the endoluminal catheter is removed downward proximal to the perforator;
iv. the vein is obliterated by delivering at least 3 pulses of pressurized overheated steam, so that the perforator cannot drain in the downward side of the superficial vein;
v. the tubular part of the endoluminal catheter is introduced distally in the superficial vein, guided upward proximal to the perforator;
vi. the vein is obliterated by delivering at least 3 pulses of pressurized overheated steam, so that the perforator cannot drain in the superficial varicose.

Any singular in this text shall correspond to a plural and reciprocally.

According to the present invention:
"usable length L" is the length of the endoluminal catheter, and more precisely of its (external) tubular part which can be introduced into the vessels. L is shown on FIGS. 3A, 3B, 4 & 7.
"thermofibrosis" means for instance occlusion or obliteration of the veins by means of endoluminal injection of steam pulses.
"flexible" means for instance a characterization by a standard mechanical test giving a flexural modulus lower than 2900 psi (corresponding to about 20 GPa).
"biocompatible" means for instance a characterization by standard biological tests such as cytotoxicity, sensitization, irritation/intracutaneous, acute systemic toxicity, hemocompatibility.
"thermically insulating" means for instance a characterization by a standard physical test giving a thermal conductivity lower than 30 BTU-in/ft$^2$-hr-° F.
"thermically resistant" means for instance a characterization by a standard physical test giving a melting point higher than 212° F. (100° C.).
"water" means for instance any pharmaceutically acceptable liquid injectable into human or animal body (vessels), notably aqueous liquid such as water, aqueous solution, physiological serum mix of water with another liquid (e.g. alcohol), possibly containing active principle and/or ingredient.
"about" means for instance an approximation of more or less 5%, preferably 1%. It should be considered that all the figures herein are given with this approximation.

BRIEF DESCRIPTION OF THE DRAWINGS

The invention and the advantages resulting from it are illustrated hereinafter by an example of embodiment in reference to the attached figures.

DETAILED DESCRIPTION

Figures 1, 2:
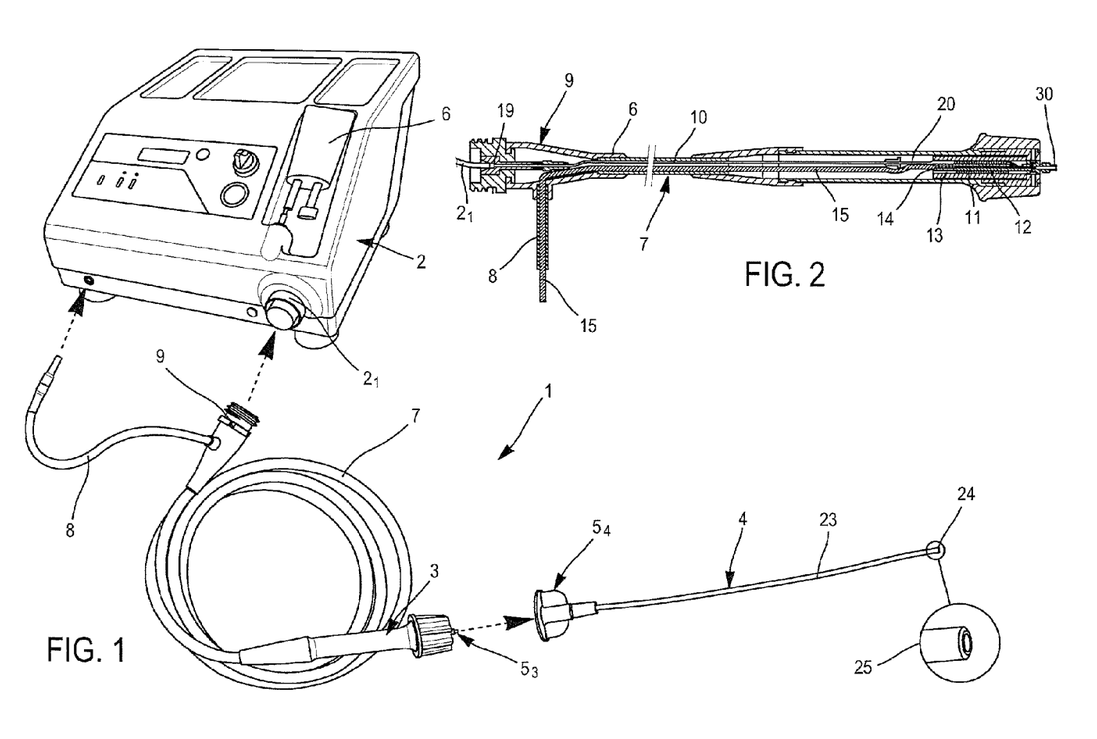
FIG. 1 is a diagram of the device according to the invention.
FIG. 2 is a cross-section in the longitudinal median plan of the hand piece pertaining to the device according to the invention.

The device shown on FIG. 1 is designed for injecting pulsed steam directly within a human or animal vessel, especially a vein. Such a device designated by reference 1 is composed of:
a water pulse generator 2 that produces micro pulses of pressurised sterile water;
a hand piece 3 that transforms pulses of water coming from the generator 2 into pulses of steam;
an endoluminal catheter 4 for delivering the steam into the vessel, especially the vein;
connection means 5 between the hand piece 3 and the endoluminal catheter 4;
a central processing unit (cpu), for instance a programmable electronic card not shown onto the attached drawings;
a sterile water storage bag 6 intended to feed the water pulse generator 2 with sterile water;
a pipe 7 which links the output of the water pulse generator 2 to the inlet of the hand piece 3;
and decompression means 50 in the extension of the outlet 30 of the hand piece 3.

The water pulse generator 2 can be as the one described in the U.S. Pat. No. 7,753,871-B2 as well as the one described in WO2006/108974-A1. For example, the water pulse generator 2 includes an injection unit comprising a pneumatic piston, a hydraulic pump both controlled by the cpu also included in the water pulse generator 2. The pneumatic piston (e.g. a large-sized pneumatic cylinder) which can also be piezoelectric or mechanical is integral with the small-sized hydraulic cylinder travelling in the chamber of the hydraulic pump where the water is pressurized. This piston and this hydraulic pump work in two phases: the filling up of the hydraulic pump with sterile water coming from the storage bag 6 and the injection of this sterile water in the pipe 7 which feeds with pulses of sterile water the hand piece 3, itself terminated in a tube fed by the water storage bag 6. The stroke, force and speed of travel of the pneumatic cylinder are programmed in the cpu to the desired frequency, volume and pressure of injection of the water pulses into the pipe 7 and the hand piece 3. This water pulse generator 2 is naturally connected to an electrical source which feeds the injection unit and the cpu as well as the hand piece 3 which should produce heat by joule effect to transform pulses of water coming from the generator 2 into pulses of steam delivered at the outlet $5_3$ of the hand piece 3. The power supply of the hand piece 3 is got by means of a cable 8 which is plugged in the front of the water pulse generator 2.

Figure 3A:
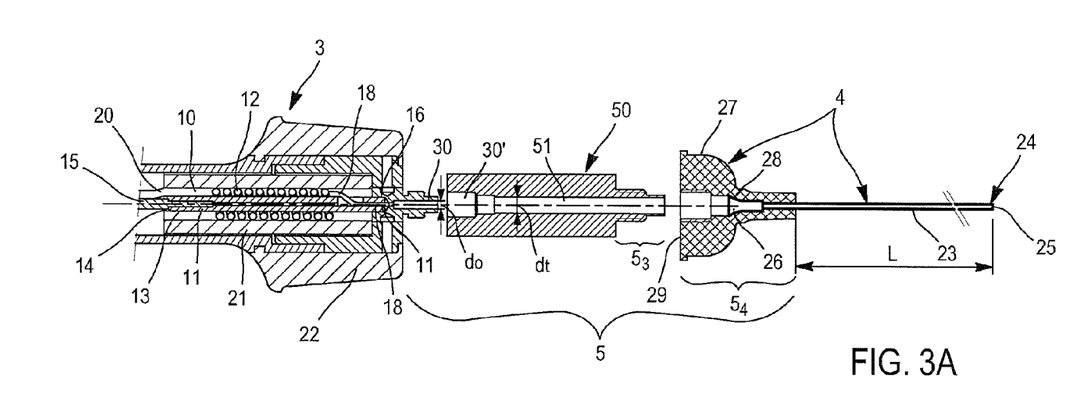
FIG. 3A is a detailed and exploded representation of the section in the longitudinal median plane of the distal terminal part of the hand piece represented on the FIG. 2 and of the endoluminal catheter.
Figure 3B:
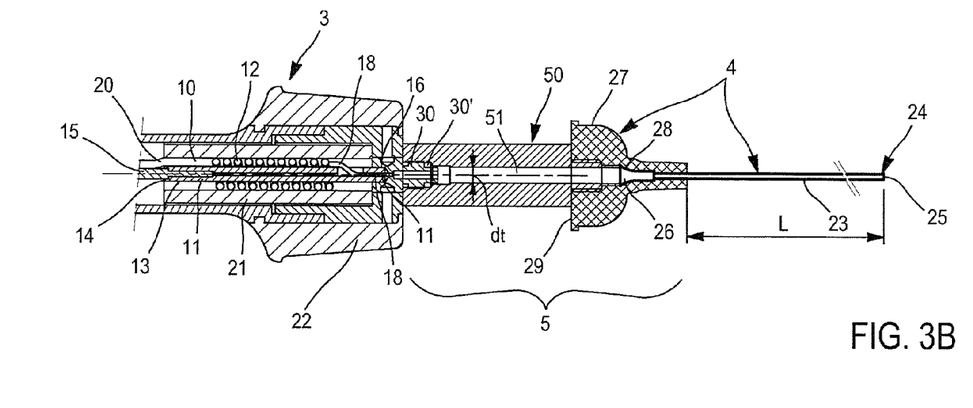
FIG. 3B is a representation analogous to FIG. 3A in which all the elements shown on FIG. 3A are assembled.

According to an important feature of the invention, the water pulse generator 2 and the hand piece 3 are designed and controlled by the cpu so that pulses of steam are made from pulses of water which volume is comprised between 5 and 70 µl, preferably 10 and 50 µl, and can be injected into the pipe 7 at a controlled period of one pulse every 0.5 to 2 seconds. The hand piece 3 which is shown in detail in FIGS. 2 & 3, is analogous to the hand piece described in columns 4 and 5, FIGS. 2 and 3 of the U.S. Pat. No. 7,753,871-B2. The attached FIGS. 2, 3A, 3B show the hand piece 3 linked (e.g by screwing), through the pipe 7's proximal end 9, to the outlet $2_1$ of the water pulse generator 2, said outlet $2_1$ supplying the water pulses produced by the injection unit. Moreover, the pipe 7's proximal end 9 is also connected to the water pulse generator 2 through the power supply cable 8. The outlet $2_1$ of the water pulse generator 2 is plugged, into the proximal end 9 of the pipe 7, to a tube 10 running through the pipe 7 and the hand piece 3. Water pulses produced by the generator 2 are transported by this tube 10 to the hand piece 3. The tube 10 is made of stainless steel and has a given resistivity, for example 72 μΩ/cm. The distal end of the tube 10 is coiled around a portion of a stainless steel tube 11 of low resistance forming a spiral 12. The portion of the stainless steel tube 11 in contact with the spiral 12 is covered by an electrical and a thermal insulating sheath 13. The proximal end 14 of the portion of the tube 11 is in contact with an electrical conductor 15 which forms the power supply 8. The distal end 16 of the portion of the tube 11 has an opening 17 allowing the distal end 18 of the spiral 12 to pass so as to be in contact with the electrical conductor formed by the portion of low resistance of the stainless steel tube 11. As FIGS. 3A and 3B show, the distal end of the portion of tube 11 has no insulating sheath, thus allowing current to pass from the stainless steel tube 11 into the spiral 12 to allow heating to occur into the spiral part of the tube 10 and not in the straight part between its proximal end 19 of the injection unit outlet and the proximal end 20 of the spiral 12. The straight part of the tube 10 has a low resistivity braided copper sheath. The screw thread of the proximal end of the pipe 7 provides the hydraulic connection which at the same time serves as electrical ground. The spiral 12 has an electrical and thermo-insulated sheath 21. Moreover the distal end of the hand piece 3 is fitted with a silicon part 22 which avoids the hand piece 3 heating up too much. The current circulates in the electrical conductor 15, in the stainless steel tube 11 of lower resistance, then in the spiral 12 to return via the tube 10 to the electrical ground at the proximal end 9 of the pipe 7.

This hand piece 3 is a heating element capable to transform pulses of water coming from the water pulse generator 2 in pulses of steam. The heating spiral 12 which is above described is close to the distal end of the hand piece 3, allowing minimal energy loss. Pulses of steam produced at the distal end 18 of the spiral 12 are propelled outside the hand piece 3 through the outlet 30 of the hand piece 3.

As shown on FIGS. 3A, 3B, 4, 4A, 4B & 7, the hand piece 3 is assembled through its outlet 30 to the endoluminal catheter 4, by the connection means 5 which comprises a distal coupling part $5_3$ (male part) which is integral with a tubular decompression chamber 50 which forms the decompression means of the steam pulses coming the outlet 30 of the hand piece 3. Said distal coupling part $5_3$ (male part) is designed to cooperate with a proximal coupling part $5_4$ (female part) of the endoluminal catheter 4. Concretely, the male part $5_3$ is intended to be introduced and fixed (e.g. by screwing) into the female part $5_4$.

In this non limitative embodiment, the tubular decompression chamber 50 is so a coupling part which is assembled in the extension of the hand piece outlet 30, this latter being tightly fixed (e.g by screwing) into a housing 30' at the proximal end of the chamber 50. The decompression chamber 50 includes a tubular part 51, wherein the steam pulses coming from the hand piece 3 are discharged. The internal diameter $d_t$ of the tubular part 51 of the decompression chamber 50 is larger than the internal diameter $d_o$ of the hand piece outlet 30. For instance, $d_t=2.5(d_o)$ and $d_t$ is about 2.5 mm. And the length of said tubular part 51 is comprised, about 20 to about 35 mm and, for instance, is about 28 mm.

In this non limitative embodiment, the proximal coupling part $5_4$ of the endoluminal catheter 4 comprises a terminal flange ring 26, as well as a socket 27 through which goes the tubular part 23 (length L) of the endoluminal catheter 4. This tubular part 23 can slide in the socket 27 as far as the flange ring 26 be stopped against an annular sealing joint 28 inside the socket 27.

Figure 4:
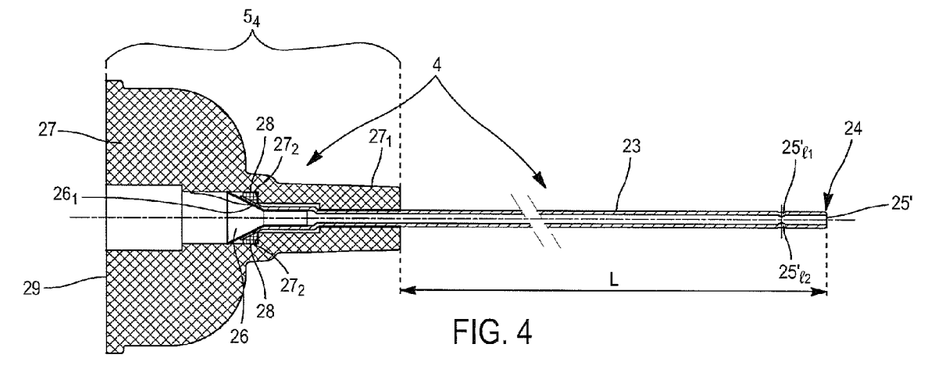
FIG. 4 is a cross-section in the longitudinal median plan of the catheter presenting a terminal and central opening plus lateral/transversal holes.
Figure 4A:
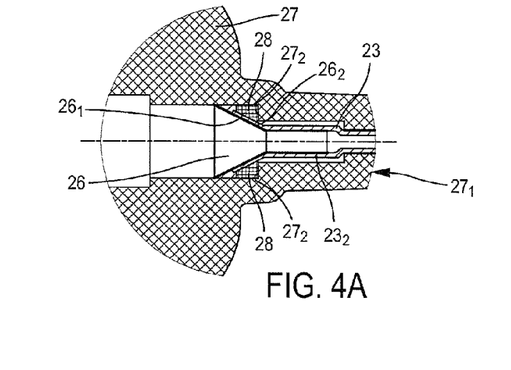
FIG. 4A is a detailed and enlarged view of the proximal coupling part of the endoluminal catheter of FIG. 4.
Figure 4B:
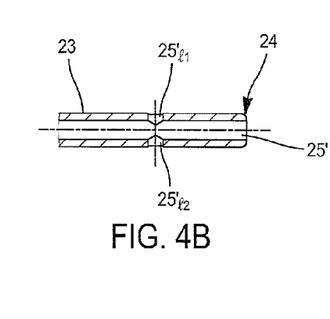
FIG. 4B is a detailed and enlarged view of the distal part of the endoluminal catheter tubular part of FIG. 4.

As it appears on FIGS. 4 & 4A, the flange ring 26 is composed of (e.g. metallic) funnel-shaped piece $26_1$ which is fixed into the proximal end part $26_2$ of the tubular part 23 of the catheter 4. Said proximal end part $26_2$ is inside the socket 27, in the nozzle $27_1$ of the socket 27. Said proximal end part $26_2$ is not included in the length L of the tubular part 23 of the catheter 4. Length L corresponds to the tubular part 23 which protrudes from the nozzle $27_1$. The annular sealing joint 28 is lodged against a shoulder $27_2$ of the distal nozzle $27_1$ and the outer face of the flange ring 26, more precisely of the proximal end part $26_2$, is blocked against the joint 28.

As shown in FIG. 3B, the screwed connection between $5_3$, the distal coupling part $5_3$ of the tubular decompression chamber 50 and the proximal coupling part $5_4$ of the socket 27, ensures a significant and longstanding compression of the sealing joint 28. The introduction by screwing of the distal coupling part $5_3$ into the proximal coupling part $5_4$ is done as far as the bottom flange 29 of the socket 27 comes into contact against the wall of the distal end of the compression chamber 50, whereas the flange ring 26 of the proximal end of the catheter 4 is in tight contact with the outlet of the decompression chamber 50. The compressed sealing joint 28 ensures the water/steam-tightness:

of the connection between the flange ring 26 and the outlet of the decompression chamber 50;

and of the connection between the flange ring 26 and the outside of the socket nozzle $27_1$ and of the proximal end part $26_2$ of the tubular part 23 of the catheter 4

Moreover, the proximal housing 30' of the chamber 50 is also tightly secured to the outlet 30 of the hand piece 3.

Figure 7:
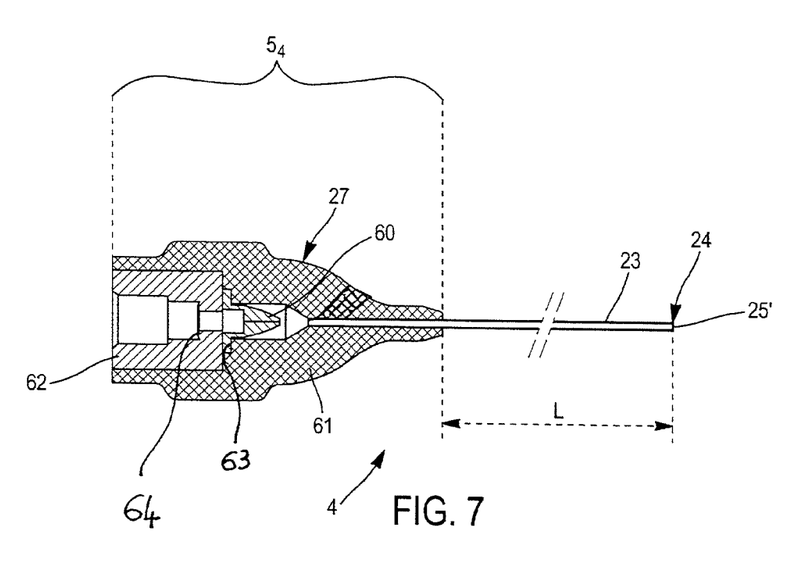
FIG. 7 is a cross-section in the longitudinal median plan of a variant of the catheter with a check-valve and a terminal and central opening.

In the variant of FIG. 7, the proximal coupling part $5_4$ of the endoluminal catheter 4 comprises a socket 27 which is extended by the tubular part 23 of the endoluminal catheter 4.

As it appears on FIG. 7, the socket 27 includes a check-valve 60 which is designed to let the steam go out of the proximal coupling part $5_4$, through the tubular part 23 of the endoluminal catheter 4, and to stop any reflux coming from the tubular part 23, in the opposite direction.

The socket 27 is moreover composed of an external covering 61 which is extended by the tubular part 23, linked by bonding, thermo-welding or preferably by over-molding.

Inside the external covering 61, there is a bonding component 62 intended to be connected with the male distal coupling part $5_3$ of the hand-piece connection means 5.

The check-valve 60 is inserted and blocked between the bonding component 62 and an internal shoulder 63 of the external covering 61.

Advantageously, the bonding component 62 includes an internal shoulder 64 having an annular boss (not shown on the FIG. 7) which improves the tightness of the connection between the male part ($5_3$) of the hand piece (7) and the female part ($5_4$) of the endoluminal catheter (4).

The tubular part 23 of the endoluminal catheter 4 is advantageously made of a non metallic plastic polymer tube, for example in PolyTetraFluoroEthylene (Teflon®) or in Poly- EtherEtherKetone (PEEK), said tube 23 being flexible, biocompatible, thermally insulating and thermally resistant. The distal end 24 of this non metallic polymer tube 23 has a terminal and central opening 25 shown on FIG. 1. This central and terminal opening 25 has a blunt, especially rounded off shape, which radius of curvature is comprised between 0.20 and 0.30 mm, e.g. 0.25 mm. At its proximal end, the tube 23 comprises the flange ring 26. Said tube 23 goes through and slides in the socket 27 which includes the female part $5_4$ of the connection means 5. This sliding is possible as far as the flange ring 26 be stopped against the sealing joint 28 located at the back and inside the female part $5_4$ of the socket 27.

The funnel-shaped piece $26_1$ of the flange ring 26 is composed of stainless steel or polymer, preferably Stainless steel AISI 304L.

The socket 27 is composed of an electrical insulating and/or thermoresistant material (polymer, ceramic . . . ), preferably Polyether ether ketone (PEEK). The sealing joint 28 is composed of polymer, preferably silicon.

According to one of the essential features of the invention, the endoluminal catheter's length L (mm) from the distal end of the socket 27 to the distal end 24 of this non metallic polymer tube 23. L is comprised between [10; 20], e.g. 15 cm.

The catheter 4 is capable to withstand high temperatures e.g. between 212° F. (100° C.) and 482° F. (250° C.), and to repeated heat pressures.

The L length protruding tubular part 23 of the catheter 4 has an outer diameter e.g. comprised between 0.1 mm and 3.0 mm, advantageously 1.07 mm and an inner diameter e.g. comprised between 0.05 mm to 2.5 mm, advantageously 0.56 mm.

In order to streamline repeated pulses over heated water vapour into the veins, the lumen of the catheter 4 has a substantially and uniformly circular cross-section from the proximal end to the distal end 25. The diameter of the lumen is e.g. comprised between 0.05 mm to 2.5 mm, preferably 0.56 mm. The outer diameter is between 0.1 and 3.0 mm, for example is 1.07 mm.

The terminal and central opening (or hole) 25 is designed to deliver the steam forward and to avoid delivering steam directly to the wall of the vein and consequently to the skin. The diameter of the central opening 25 is substantially equal to the inner diameter of the catheter 4 and so is in direct continuity to the distal end and the proximal end of the catheter 4. It allows the delivery of steam all within and along the lumen of the vein. The rounded off or blunt shape of this central makes it possible to introduce safely the catheter 4 into tortuous tributary veins, hindering perforations or any traumatism of the wall of the vein.

In case of dilated veins, for example veins presenting pseudo aneurysmal dilatation and/or veins having a diameter greater than e.g. 3 mm, the catheter 4 is designed with transversal holes $25_{e_1}$, $25_{e_2}$ in addition to the terminal and central opening 25', as shown on FIG. 4, in which the same references as in FIGS. 3A & 3B designate the same elements. This allows to deliver steam in a multidirectional way. As this feature allows also to decrease the pressure of the water steam coming from the heating element, there is no risk of vein wall perforation and/or skin burn.

Preferably, the endoluminal catheter 4 is a single use sterile unit.

Said catheter 4 (tube 23) can be introduced percutaneously into the veins to deliver locally the right amount of energy provided by the steam to obliterate the veins.

These 10 cm/20 cm long catheters 4 with a unique and central hole 25 at its distal end is adapted to the small diameter and to the tortuosity of the veins, tributaries and perforators.

The introduction of the catheter 4 (tube 23) into the vein is done by means of introducers 100 which are punctured into the vessel and more particularly into the tributaries or perforators vein to be treated.

Figure 5:
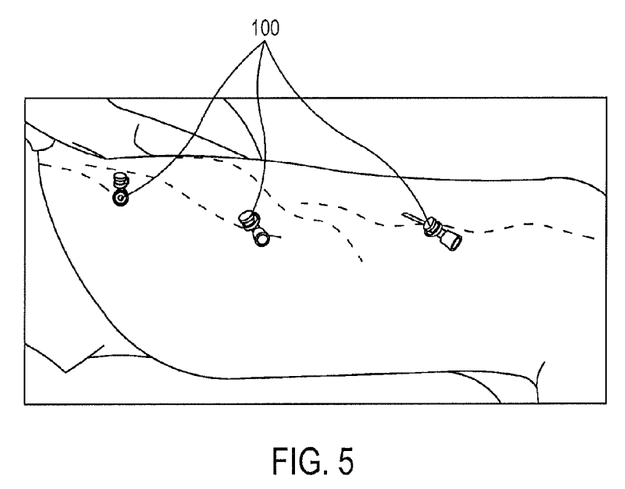
FIG. 5 is a schematic view of the leg of a patient with varicosities to be treated by means of the device according to the invention, several introducers being punctured in several injection points of the ill vein.

The Treatment of Tributaries is Described Hereinafter in Reference to FIGS. 5 & 6.

The catheter 4 (tube 23) is introduced into a patient and positioned within the section of the vein to be treated through multiple punctures. This puncturing of these introducers 100 is done by means of a needle positioned in a small catheter of 5 cm long constituting the introducers 100. Once these introducers 100 are punctured into the veins to be treated, forming several injection points, the endoluminal catheter 4 (tube 23) can be introduced into the vein through the introducers 100, as shown in FIG. 6. The catheter has a length and a diameter sufficient to deliver pressurized overheated steam towards the vein, and the surrounding venous tissue that becomes heated and begins to shrink. The catheter remains active until there has been sufficient shrinkage of the vein. The extent of shrinkage of the vein can be detected by Doppler echography.

So for treating these veins, the catheter 4 is entered under echo guidance, and stays in place while several pulses of steam are delivered consecutively. One can feel the steam travelling along the vein trough the skin by applying one hand over the anatomical territory of the vein.

Thus, 6 to 10 cm segments can be treated, by delivering e.g. a maximum of 6 pulses at the same catheter location to avoid overheating at this level. Local anesthesia is used: e.g. 5 to 10 cc are infiltrated between the vein and the skin. Skin cooling can be substituted or conjugated to such an injection of anesthetic, with skin temperatures down to e.g. 39.2/42.8° F. (4/6° C.).

The vein could still be visible under the skin, but should not be painful. Disappearance will take several months, up to 6 if the vein was large.

Post-operatively, it is useful to control the patient at 1 or 2 weeks: if a lot of thrombus is seen at the Duplex examination, a puncture can be made with a 21 G needle for evacuation.

Usually, no pain and no inflammatory reaction are experienced, a significant advantage when compared to foam sclerosis.

The Treatment of Perforators is Described Hereinafter

There are two methods according to the invention: direct and indirect obliteration Direct obliteration is feasible if the perforator is long and tortuous (more than 2 cm): under echo guidance the catheter is introduced into the perforator, at least 2 cm from the deep vein. For instance, 3 pulses are emitted, then the catheter is retracted 1 cm and 3 other pulses are emitted.

Indirect obliteration is safer for short perforators (less than 2 cm): the catheter is introduced distally in the superficial vein, guided upstream or downstream proximal to the perforator. The vein is obliterated by means of pulses of steam. The catheter is then moved downstream or upstream respectfully proximal to the perforator. The vein is then obliterated by means of pulses of steam. Thanks to these downstream and upstream obliteration, the perforator cannot drain into the superficial varicose.

Figure 6:
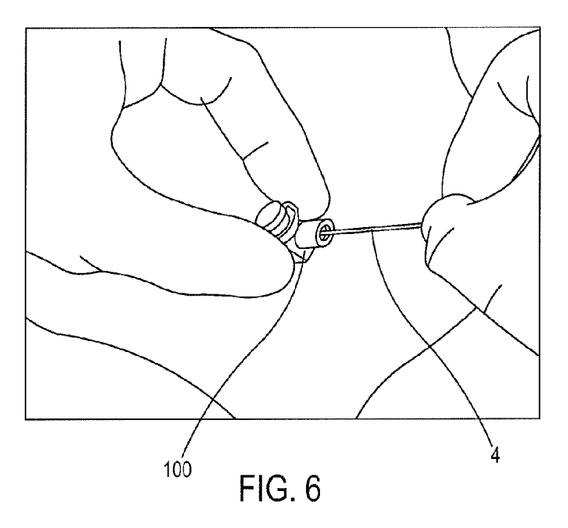
FIG. 6 shows the introduction of the endoluminal catheter of the device according to the invention into one of the introducers shown on FIG. 5.

In both methods the catheter 4 (tube 23) is introduced into the veins through an introducer 100 (as shown in FIG. 6).

The invention claimed is:

1. A method for treating tributaries comprising using a device for injecting pulsed steam into human or animal vessel, the device including:
 a water pulse generator that produces micro pulses of pressurized sterile water;

a hand piece that transforms pulses of water coming from the generator into pulses of steam;

an endoluminal catheter for delivering the steam into the vessel;

connection means between the hand piece and the endoluminal catheter;

and a programmable central processing unit (cpu) to control the water pulse generator and the hand piece;

wherein
- a. the endoluminal catheter comprises a tubular part which length L (in cm) is comprised between one of the following inclusive ranges: [1; 30], [2; 28], [3; 27], [4; 26], [5; 25], [6; 24], [8; 22], [10; 20];
- b. the tubular part of the endoluminal catheter is made of a flexible, biocompatible, thermally insulating and thermically resistant non-metallic material or polymer;
- c. the distal end of the endoluminal catheter has a terminal and central opening;

the method further comprising:
- i. the tubular part of the endoluminal catheter is introduced into a patient and positioned within the section of the vein to be treated through multiple punctures; each of them corresponding to a given segment of vein to be treated;
- ii. several pulses of pressurized overheated steam are delivered consecutively towards the vein;
- iii. the tubular part of the endoluminal catheter remains active until there has been sufficient shrinkage of the vein;
- iv. the extent of shrinkage of the vein is detected by appropriate detection means;

and wherein the segments' length is 4 to 12 cm.

2. A method for treating tributaries comprising using a device for injecting pulsed steam into human or animal vessel, the device including:

a water pulse generator that produces micro pulses of pressurized sterile water;

a hand piece that transforms pulses of water coming from the generator into pulses of steam;

an endoluminal catheter for delivering the steam into the vessel;

connection means between the hand piece and the endoluminal catheter;

and a programmable central processing unit (cpu) to control the water pulse generator and the hand piece;

wherein
- a. the endoluminal catheter comprises a tubular part which length L (in cm) is comprised between one of the following inclusive ranges: [1; 30], [2; 28], [3; 27], [4; 26], [5; 25], [6; 24], [8; 22], [10; 20];
- b. the tubular part of the endoluminal catheter is made of a flexible, biocompatible, thermally insulating and thermically resistant non-metallic material or polymer;
- c. the distal end of the endoluminal catheter has a terminal and central opening;

the method further comprising:
- i. the tubular part of the endoluminal catheter is introduced into a patient and positioned within the section of the vein to be treated through multiple punctures; each of them corresponding to a given segment of vein to be treated;
- ii. several pulses of pressurized overheated steam are delivered consecutively towards the vein;
- iii. the tubular part of the endoluminal catheter remains active until there has been sufficient shrinkage of the vein;
- iv. the extent of shrinkage of the vein is detected by appropriate detection means;

and wherein local anesthesia is carried out by skin cooling, with skin temperatures down to 39.2/42.8° F. (4/6° C.).

3. A method for treating by direct obliteration, a tortuous perforating vein longer than 2 cm and extending between a superficial vein and a deep vein, said method comprising using a device for injecting pulsed steam into human or animal vessel, the device including:

a water pulse generator that produces micro pulses of pressurized sterile water;

a hand piece that transforms pulses of water coming from the generator into pulses of steam;

an endoluminal catheter for delivering the steam into the vessel;

connection means between the hand piece and the endoluminal catheter;

and a programmable central processing unit (cpu) to control the water pulse generator and the hand piece;

wherein
- a. the endoluminal catheter comprises a tubular part which length L (in cm) is comprised between one of the following inclusive ranges: [1; 30], [2; 28], [3; 27], [4; 26], [5; 25], [6; 24], [8; 22], [10; 20];
- b. the tubular part of the endoluminal catheter is made of a flexible, biocompatible, thermally insulating and thermically resistant non-metallic material or polymer;
- c. the distal end of the endoluminal catheter has a terminal and central opening;

the method further comprising:
- i. the tubular part of the endoluminal catheter is introduced under echo guidance in the perforator, at least 2 cm from the deep vein,
- ii. at least 3 pulses of pressurized overheated steam are delivered,
- iii. then the tubular part of the endoluminal catheter is removed of a distance of about 1 cm and 3 other pulses are emitted.

4. A method for treating by indirect obliteration, a 2 cm long or less perforating vein extending between a superficial vein and a deep vein, said method comprising using a device for injecting pulsed steam into human or animal vessel, the device including:

a water pulse generator that produces micro pulses of pressurized sterile water;

a hand piece that transforms pulses of water coming from the generator into pulses of steam;

an endoluminal catheter for delivering the steam into the vessel;

connection means between the hand piece and the endoluminal catheter;

and a programmable central processing unit (cpu) to control the water pulse generator and the hand piece;

wherein
- a. the endoluminal catheter comprises a tubular part which length L (in cm) is comprised between one of the following inclusive ranges: [1; 30], [2; 28], [3; 27], [4; 26], [5; 25], [6; 24], [8; 22], [10; 20];
- b. the tubular part of the endoluminal catheter is made of a flexible, biocompatible, thermally insulating and thermically resistant non-metallic material or polymer;
- c. the distal end of the endoluminal catheter has a terminal and central opening;

the method further comprising:
- i. the tubular part of the endoluminal catheter is introduced distally in the superficial vein, guided upward proximal to the perforator;

ii. the vein is obliterated by delivering at least 3 pulses of pressurized overheated steam, so that the perforator cannot drain in the upward side of the superficial vein;
iii. the tubular part of the endoluminal catheter is removed downward proximal to the perforator;
iv. the vein is obliterated by delivering at least 3 pulses of pressurized overheated steam, so that the perforator cannot drain in the downward side of the superficial vein.

\* \* \* \* \*